United States Patent [19]

McChesney et al.

[11] Patent Number: 5,225,562

[45] Date of Patent: Jul. 6, 1993

[54] METHOD OF PREPARING (+)-DEOXOARTEMISININ AND SELECTED ANALOGUES OF (+)-DEOXOARTEMISININ

[76] Inventors: James D. McChesney, Rte. 1, Box 340, Etta, Miss. 38627; Mankil Jung, 81 Jeff St., Oxford, Miss. 38655

[21] Appl. No.: 565,470

[22] Filed: Aug. 10, 1990

[51] Int. Cl.$^5$ ................... C07D 491/18; C07D 325/00
[52] U.S. Cl. ..................................... 546/270; 549/348
[58] Field of Search ............... 549/348; 514/450, 338; 546/270

[56] References Cited

U.S. PATENT DOCUMENTS 4,920,147  4/1990  McChesney et al. ............... 514/450

FOREIGN PATENT DOCUMENTS 0330520  8/1989  European Pat. Off. ............ 549/348
0362730  4/1990  European Pat. Off. ............ 549/348

OTHER PUBLICATIONS

Jung et al. "Synthesis and antimalarial activity of (+) deoxoartemisinin" *J. Med. Chem.* 1990 vol. 33 pp. 1516–1518.
Jung et al "A Short and Stereospecific Synthesis of . . . " *Tetrahedron Letters*, vol. 30 No. 44 pp. 5973–5976 (1989).
Bustas et al. "Stereospecific Synthesis of (+−homo-deoxo-artemisinin" *Heterocycles* vol. 29 No. 12 pp. 2273–2277 (1989).

*Primary Examiner*—C. Warren Ivy
*Assistant Examiner*—A. A. Owens
*Attorney, Agent, or Firm*—William D. Stokes

[57] ABSTRACT

This invention is a new method for preparing compounds useful as antimalarial agents having the formula;

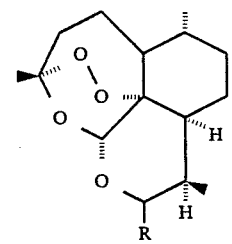

wherein R is hydrogen, a linear, branched or cyclo lower alkyl group having 1 to 8 carbon atoms; aminoalkyl; branched aminoalkyl; hydroxyalkyl; alkylcarboxylate or alkylbenzoate groups having 1 to 5 carbon atoms in the alkyl chains; aryl; alkoxy-substituted aryl; heteroaryl; and pyridinium groups. The method comprises treating artemisinic acid with a methylating agent followed by a stereoselective reduction of the methylated compound, subjecting the reduced compound to a Grignard addition followed by chiral photoxidation with subsequent treatment with a cyclization agent.

24 Claims, No Drawings

METHOD OF PREPARING (+)-DEOXOARTEMISININ AND SELECTED ANALOGUES OF (+)-DEOXOARTEMISININ

BACKGROUND OF THE INVENTION

Malaria is the number one infectious disease in the world today. Notwithstanding that it was believed that malaria was close to becoming eradicated in the 1960's with the use of quinine, chloroquine and DDT, it was not. Rather malaria is an ever growing problem throughout the world. Approximately 200 million people in endemic areas are infected annually. Worldwide, over two million people die each year from malaria. This shocking reality is due in part to the emergence of drug resistant strains of *Plasmodium falciparum*, the most lethal malarial parasite known to date. More specifically, a high percentage of malaria today is caused by chloroquine-resistant *Plasmodium falciparum*.

Artemisinin (Qinghaosu), first isolated by the Chinese from the leaves of *Artemisia annua* in 1972, is known to be a fast acting, safe and effective drug against chloroquine-resistant and sensitive strains of *Plasmodium falciparum*, as well as against cerebral malaria. No side effects, common to many synthetic antimalarials, have been reported by the Chinese during the past six years of clinical use of artemisinin. Unfortunately, one of the disadvantages o artemisinin is that the compound is only sparingly soluble in either water or oils and thus not readily absorbable by the gastrointestinal tract. Another disadvantage of the drug resides is the fact that large doses (3×400 mg/day per patient) of the drug are required for therapetic efficacy. A more ideal drug with enhanced antimalarial activity and improved physical and bioavailability properties is an urgent need to treat chloroquine-resistant malaria.

In U.S. Pat. No. 4,920,147 to McChesney and Jung, there is described a novel method of preparing deoxoartemisinin comprising essentially a one-step process of directly reducing artemisinin, derived from the leaves of *Artemisia annua*, with a mild reducing agent followed by refluxing the mixture to yield the deoxoartemisinin.

The structural complexity of artemisinin, particularly the presence of a peroxide bridge which must be preserved for drug efficacy and chemically sensitive lactone ring, has rendered the preparation of derivatives of artemisinin without a carbonyl function extremely difficult. This difficulty is one of the reasons that the method described in the aforementioned patent represents such an advance in the art; however, the yields of deoxoartemisinin produced by the method of the patent is limited by the availability of artemisinin. Moreover, there has not been any practical method of preparing derivatives of (+)-deoxoartemisinin and compounds which are analogues of deoxoartemisinin useful as antimalarial agents. The new compounds are producible in extremely large quantities from the same quantity of leaves of *Artemisia annua* required to prepare the small amounts of deoxoartemisinin prepared using the method of the prior art. In accordance with the method of the invention, (+)-deoxoartemisinin may be prepared simply and practically in quantities substantially six times greater than the known method using as a starting material artemisinic acid derived from the leaves of *Artemisia annua*.

SUMMARY OF THE INVENTION

The invention is a new method of preparing (+)-deoxoartemisinin and its homologues and analogs, and contemplates using as a starting material artemisinic acid derived from the the leaves of *Artemisia annua*. Artemisinic acid enables the preparation of great quantities of (+)-deoxoartemisinin and its useful analogues from the readily available, naturally occurring starting material. While it was known that *Artemisia annua* contained at least six times more artemisinic acid than artemisinin, there was no known method of preparing (+)-deoxoartemisinin and analogues thereof from the acid. This invention provides a simple and practical method of preparing (+)-deoxoartemisinin and analogues thereof from artemisinic acid in great quantities as contrasted with the known method of using artemisinin as a starting material as taught in the art.

The compound (+)-deoxoartemisinin is represented by the structural formula:

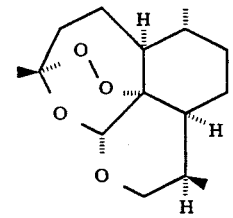

The useful analogues of (+)-deoxoartemisinin of this invention have the following structural formula:

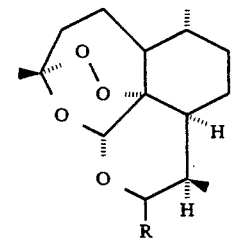

wherein R is a linear, branched or cyclo lower alkyl group having 1 to 8 carbon atoms; aminoalkyl; branched aminoalkyl; hydroxyalkyl; alkylcarboxylate or alkylbenzoate groups having 1 to 5 carbon atoms in the alkyl chains; aryl; alkoxy-substituted aryl; heteroaryl; and pyridinium groups.

DETAILED DESCRIPTION OF THE INVENTION

The artemisinic acid used in the examples of·the invention was isolated from the leaves of *Artemisia annua* in accordance with the method of Farouk S. ElFeraly and Hala N. ElSohly described in co-pending application Ser. No. 07/208,763. The invention comprises the steps of methylation of artemisinic acid to form methylartemisinate, where (+)-deoxoartemisinin is the desired final product, the methylate is subjected to stereoselective direct reduction, chiral photoxidation followed by cyclization. Where a specific analog is the desired end product, the methylate is reduced to form the aldehyde, then a Grignard addition of the desired R group which compound is subjected to chiral photoxidation followed by cyclization forming the desired analogue.

The artemisinic acid used in the examples of the invention was prepared as described in Example I.

EXAMPLE I

Dried unground leaves of *Artemisia annua* (250g) was extracted by continuous hot percolation over a period of 48 hours using n-hexane as a solvent. The solvent free extract (19.5g, 7.8%) was partitioned with n-hexane and 20% aqueous acetonitrile, presaturated with each other, using 12 ml hexane per gram extract and one third of this amount (4 ml/g) of the 20% aqueous acetonitrile phase. Partitioning of the hexane phase between 20% aqueous acetonitrile was repeated two additional times using the same solvent ratio. The combined 20% aqueous acetonitrile was back-washed using 10% of its volume with presaturated hexane (24 ml). Sodium chloride (7g/100 ml of 20% aqueous acetonitrile) was added to remove the water. Evaporation of the acetonitrile *in vacuo* provided 6.7g of an oily yellowish-brown residue. About 650 mg of artemisinic acid was crystallized from this acetonitrile phase. Column chromatography of the residue was conducted using Machery Nagel silica gel 60 (Brinkmann, mesh size 70-270) in the ratio of 1:10. The eluting system comprising 10% ethyl acetate/hexane (1.0 column volume), followed by 15% ethyl acetate/hexane (1.0 column volume1 and 20% ethyl acetate/hexane (one and one-half column volume), at filtration flow rates, yielded artemisinic acid followed by artemisinin. Artemisinic acid (900 mg) was isolated in the fraction eluted with 10-15% ethyl acetate/hexane (1.66 column volume).

Example II illustrates the simple and practical method of the invention for preparing (+)-deoxoartemisinin from artemisinic acid.

EXAMPLE II

Artemisinic acid (40g, 170 mmol) prepared in accordance with Example I was methylated with diazomethane generated from N-methyl-N-nitroso-p-toluenesulfonamide (85g, 400 mmol) in diethylether (800 ml) at 0° C. to afford (39g) of methylartemisinate.

A solution of the methylartemisinate (13.5g; 55.5 mmol) in diethylether (140 ml) was added to a solution of LiAlH4 (8.42g; 227 mmol)(16 eq.) and NiCl2.6H2O (8.25g; 34.7 mmol)(0.6 eq.) in anhydrous diethylether at room temperature under nitrogen-atmosphere. The reaction mixture was stirred for one hour at room temperature. 1,500 ml diethylether and 10 ml brine was added to the mixture and stirred for one hour at room temperature. 80g of anhydrous MgSO4 was added to the mixture with continuous stirring. The heterogenous mixture obtained was filtered and the residue was washed with diethylether. The filtrate was evaporated *in vacuo* to yield a yellow oil which was subjected to flash column chromatography (silica gel H for thin layer chromatography without gypsum)(hexane/ethyl acetate) yielding 5.9g of dihydroartemisinyl alcohol in the form of colorless needles having the formula:

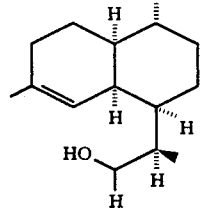

A solution of dihydroartemisinyl alcohol (2.0g. 9 mmol) and methylene blue (150 mg) in methylene chloride (70 ml) was cooled to −78° C. which mixture was irradiated with a 450 watt medium pressure mercury vapor lamp while oxygen was bubbling through the solution. After four hours, the solvent was removed *in vacuo* yielding an oily substance which was dissolved in a mixture (1:1) of hexane and ethyl acetate followed by filtering through a silica gel bed. The solvent was evaporated *in vacuo* leaving a brown oil which was dissolved in hexane (40 ml). Dowex 50W resin (150 mg./strongly acidic) was added and the mixture stirred at room temperature. Evaporation *in vacuo* yielded a yellowish oil. Purification by flash column chromatography (silica gel in 4 parts hexane to 1 part ethyl acetate) followed by recrystallization from petroleum ether yielded 0.44g of pure (+)-deoxoartemisinin.

EXAMPLE III

Artemisinic acid (40g, 170 mmol) prepared in accordance with Example I was methylated with diazomethane generated from N-methyl-N-nitroso-p-toluenesulfonamide (85g. 400 mmol) in diethylether (800 ml) at 0° C. to afford 39g of methylartemisinate. Lithium borohydride (1.75g, 80.4 mmol) was added to the solution of the methyl artemisinate (10g, 40.2 mmol) and NiCl2. 6H2O (4.78g. 20.1 mmol) in anhydrous diethylether (200 ml) at room temperature under nitrogen atmosphere. Then the mixture was stirred at room temperature for 30 minutes. Water (500 ml) was added and the aqueous phase was extracted with diethylether (500 ml). The extracts were dried over anhydrous MgSO4 and the filtrate was evaporated *in vacuo* to yield 8.1 g of methyl dihydroartemisinate as yellow oil having the formula:

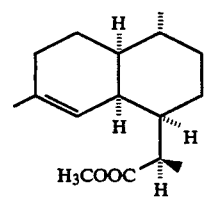

Diisobutylaluminum hydride (28.2 ml of a 1 Molar solution in CH2Cl2) was added dropwise to a cooled (−78° C.) solution of methyl dihydroartemisinate (5.0 g) in methylene chloride (150 ml) under nitrogen atmosphere. The mixture was stirred at −78° C. for 2 hours. Anhydrous methanol (5 ml) was added to quench the reaction, and the reaction mixture was poured into a mixture of 10% sodium tartrate solution (170 ml) and CH2Cl2 (60 ml). The CH2Cl2 extracts were dried over anhydrous MgSO4 and the filtrate was evaporated *in vacuo* to yield 4.8 g of dihydroartemisinyl aldehyde as a colorless oil having the formula:

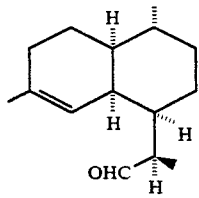

Dry magnesium (700 mg, 28.8 mmol) was placed in a three-neck round bottom flask equipped with a condenser and an equilizing pressure funnel under nitrogen atmosphere. Then anhydrous diethylether (20 mL) was added and after that a solution of n-butylbromide (3.42g, 24.9 mmol, 5.4 eq.) in anhydrous diethylether (20 mL) was added dropwise. A vigorous gas evolution was seen and the reaction mixture was cooled in a water bath. Then the reaction mixture was stirred 30 minutes at room temperature. A solution of dihydroartemisinyl aldehyde (1.0 g, 4.54 mmol) in anhydrous diethylether (10 mL) was added dropwise and the reaction mixture was stirred at room temperature for 40 minutes. The reaction mixture was poured into a cooled (ice bath) saturated solution of NH$_4$Cl (100 mL). Organic and aqueous phases were separated and aqueous phase was extracted with diethylether (3 times of 40 mL). Organic phases were combined, washed with water (40 mL) and were dried over anhydrous MgSO$_4$. Then the solvent was evaporated in vacuo to give an oily crude product (1.4 g), which was purified by flash chromatography (hexane/ethyl acetate 9:1) to afford the desired 12-n-butyldihydroartemisinyl alcohol as an oil (1.05 g, 93% yield) having the formula:

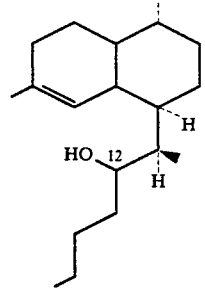

A cooled solution (−78° C.) of 12-n-butyldihydroartemisinyl alcohol (1.2 g, 3.6 mmol) and methylene blue (15 mg) in methylene chloride (18 mL) was irradiated with a 450 watt medium-pressure mercury vapor lamp while oxygen was bubbled through the solution. After 4 hours, the solvent was removed in vacuo to afford an oily residue. The residue was dissolved in a mixture of hexane and ethyl acetate (1:1) and filtered through a silica gel bed. Solvent was evaporated in vacuo and a brown oil was obtained. This oil was dissolved in hexane (30 mL) and Dowex 50W resin (150 mg, strongly acidic) was added and the resultant mixture was stirred at room temperature for four hours. Evaporation in vacuo afforded a yellow oil. Purification by flash column chromatography (silica gel with hexane/ethyl acetate 4:1) afforded 12-n-butyldeoxoartemisinin as colorless oil having the formula:

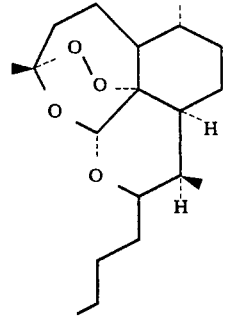

EXAMPLE IV

Artemisinic acid (0.27 g, 1.14 mmol) prepared in accordance with Example I was methylated with diazomethane generated from N-methyl-N-nitroso-p-toluenesulfonamide (0.57g, 2.67 mmol) in diethylether (6 ml) at 0° C. to afford 0.26g of methylartemisinate. Lithium borohydride (0.045g, 2.08 mmol) was added to the solution of the methyl artemisinate (0.26g, 1.04 mmol) and NiCl$_2$. 6H$_2$0 (0.124g, 0.52 mmol) in anhydrous diethylether (5 ml) at room temperature under nitrogen atmosphere. Then the mixture was stirred at room temperature for 30 minutes. Water (14 ml) was added and the aqueous phase was extracted with diethylether (14 ml). The extracts were dried over anhydrous MgSO4 and the filtrate was evaporated in vacuo to yield 0.21 g of methyl dihydroartemisinate as yellow oil having the formula:

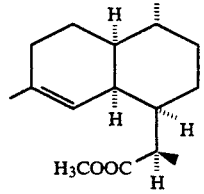

Diisobutylaluminum hydride (1.175 ml of a 1 Molar solution in CH$_2$Cl$_2$) was added dropwise to a cooled (−78° C.) solution of methyl dihydroartemisinate (0.21 g) in methylene chloride (6.25 ml) under nitrogen atmosphere. The mixture was stirred at −78° C.) for 2 hours. Anhydrous methanol (0.2 ml) was added to quench the reaction, and the reaction mixture was poured into a mixture of 10% sodium tartrate solution (7 ml) and CH$_2$Cl$_2$ (2.5 ml). The CH$_2$Cl$_2$ extracts were dried over anhydrous MgSO$_4$ and the filtrate was evaporated in vacuo to yield (0.2g) of dihydroartemisinyl aldehyde as a colorless oil having the formula:

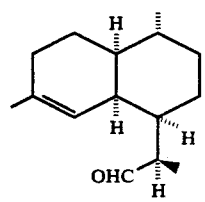

Dry magnesium (140 mg, 5.8 mmol) was placed in a three-neck round bottom flask equipped with a condenser and an equilizing pressure funnel under nitrogen atmosphere. Then anhydrous diethylether (4 mL) was added and after that a solution of allylbromide (580 mg, 4.86 mmol) in anhydrous diethylether (4 mL) was added dropwise. A vigorous gas evolution was seen and the reaction mixture was cooled in a water bath. Then the reaction mixture was stirred 30 minutes at room temperature. A solution of dihydroartemisinyl aldehyde (0.2g, 0.9 mmol) having the formula:

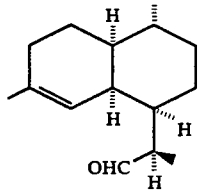

in anhydrous diethylether (2 mL) was added dropwise and the reaction mixture was stirred at room temperature for 40 minutes. The reaction mixture was poured into a cooled (ice bath) saturated solution of NH₄Cl(20 mL). Organic and aqueous phases were separated and aqueous phase was extracted with diethylether (3 times of 8 mL). Organic phases were combined, washed with water (10 mL) and were dried over anhydrous MgSO₄. Then the solvent was evaporated in vacuo to give an oily crude product, which was purified by flash chromatography (hexane/ethyl acetate 9;1) to afford the desired 12-allyldihydroartemisinyl alcohol as a colorless oil (151 mg) having the formula:

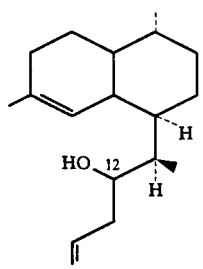

A solution of 12-allyldihydroartemisinyl alcohol (100 mg, 0.27 mmol) in anhydrous tetrahydrofuran (2.5 ml) at room temperature under nitrogen atmosphere was treated with a solution of 9-borabicyclo [3,3,1] nonane (82 mg, 0.68 mmol) in hexane and the mixture was stirred for 24 hours. Then 2N aqueous NaOH (0.96 ml) and 30% H₂O₂ (0.34 ml) were added and the mixture was heated at 50° C. for 1 hour. The mixture was diluted with diethylether (30 ml) and was dried over MgSO₄. Evaporation in vacuo afforded a yellow oil which was subjected to flash column chromatography (hexane/ethyl acetate 4:1) yielding 12-(3'-hydroxypropyl) dihydroartemisinyl alcohol (81 mg) as a yellow oil having the formula:

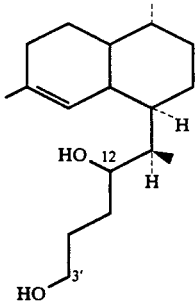

A cooled (−78° C.) solution of 12-(3'-hydroxypropyl) dihydroartemisinyl alcohol (100 mg. 0.36 mmol) and methylene blue (4 mg) in methylene chloride (2 mL) was irradiated with a 450 watt medium-pressure mercury vapor lamp while oxygen was bubbled through the solution. After 4 hours, the solvent was removed in vacuo to afford an oily residue. The residue was dissolved in a mixture of hexane and ethyl acetate (1:1) and filtered through a silica gel bed. Solvent was evaporated in vacuo and a brown oil was obtained. This oil was dissolved in hexane (3 mL) and Dowex 50W resin (15 mg, strongly acidic) was added and the resultant mixture was stirred at room temperature for 4 hours. Evaporation in vacuo afforded a yellow oil. Purification by flash column chromatography (silica gel with hexane/ethyl acetate 4:1) afforded 12-(3'-hydroxypropyl) deoxoartemisinin as a colorless oil having the formula:

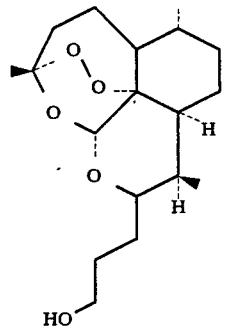

Using the method of the preceding Examples III and IV, the following compounds were prepared which exemplify compounds of the invention wherein R is a cyclo lower alkyl group having 1 to 8 carbon atoms.

EXAMPLE V 12-methylcyclopentyldeoxoartemisinin.

EXAMPLE VI 12-cyclopentyldeoxoartemisinin.

EXAMPLE VII 12-cyclohexyldeoxoartemisinin.

Using the method of the preceding Examples III and IV, the following compounds were prepared which exemplify compounds of the invention wherein R is an aminoalkyl group having 1 to 5 carbon atoms in the alkyl chain.

EXAMPLE VIII 12-(3'-dimethylaminopropyl) deoxoartemisinin.

EXAMPLE IX 12-(3'-diethylaminopropyl) deoxoartemisinin.

Using the method of Examples III and IV, the following compounds were prepared which exemplify compounds of the invention wherein R is an alkylcarboxylate group having 1 to 5 carbon atoms in the alkyl chain.

EXAMPLE X 12-(2'-carboxyethyl) deoxoartemisinin.

EXAMPLE XI 12-(carboxymethyl) deoxoartemisinin.

Using the method of Examples III and IV the following compounds were prepared which exemplify compounds of the invention wherein R is an alkylbenzoate group having 1 to 5 carbon atoms in the alkyl chain.

EXAMPLE XII 12-(4'-carboxyphenethyl) deoxoartemisinin.

EXAMPLE XIII 12-(3'-carboxyphenethyl) deoxoartemisinin.

Using the method of Examples III and IV, the following compound was prepared which exemplify compounds of the invention wherein R is an aryl group.

EXAMPLE XIV 12-phenyldeoxoartemisinin.

Using the method of Examples III and IV, the following compound was prepared which exemplify compounds of the invention wherein R is an alkoxy substituted aryl group.

EXAMPLE XV 12-(3',4'-dimethoxybenzyl) deoxoartemisinin.

Using the method of Examples III and IV, the following compound was prepared which exemplify compounds of the invention wherein R is a heteroaryl group.

EXAMPLE XVI 12-(3'-pyridylmethyl) deoxoartemisinin.

Using the method of Examples III and IV, the following compound was prepared which exemplify compounds of the invention wherein R is a pyridinium group.

EXAMPLE XVII

N-(12-n-propyl deoxoartemisinin) pyridium chloride.

In addition to methylene blue, hematoporphyrin and rose bengal may be successfully used in the photosensitizing step of the invention. It will be appreciated that many other chemical reagents such as reducing cyclizing and reduction agents may be substituted for use in the steps of the method of the invention without departing from the spirit and scope of the invention.

We claim:

1. The method of preparing compounds having the formula:

wherein R is hydrogen; linear, branched or cyclo groups having 1 to 8 carbon atoms; aminoalkyl; branched aminoalkyl; hydroxyalkyl; alkylcarboxylate and alkylbenzoate groups having 1 to 5 carbon atoms in the alkyl chain; aryl; alkoxy-substituted aryl; alkyl pyridyl and alkylpyridinium groups comprising the steps of reacting artemisinic acid with a methylating agent, stereoselectively reducing the methylated compound, subjecting the aldehyde to a Grignard addition producing an alcohol, subjecting the alcohol to a chiral photoxidation, and treating preventing the chiral photoxidation product with a cyclization agent.

2. The method of claim 1 wherein the photosensitizing agent is methylene blue.
3. The method of claim 1 wherein the photosensitizing agent is hematoporphyrin.
4. The method of claim 1 wherein the photosensitizing agent is rose bengal.
5. The method of claim 1 wherein the methylating agent is diazomethane.
6. The method of claim 1 wherein the stereoselective reducing agent is lithium borohydride.
7. The method of claim 1 wherein the stereoselective reducing agent is diisobutylaluminum hydride.
8. The method of preparing (+)-deoxoartemisinin comprising the steps of reacting artemisinic acid with a methylating agent, stereoselectively reducing the methylated compound, subjecting the aldehyde to a Grignard addition producing an alcohol, subjecting the alcohol to a chiral photoxidation, and treating the chiral photoxidation product with a cyclization agent.
9. Compounds having the formula:

wherein R is a linear, branched or cyclo lower alkyl groups having 1 to 8 carbon atoms; aminoalkyl; branched aminoakyl; hydroxyalkyl; alkylcarboxylate and alkylbenzoate groups having 1 to 5 carbon atoms in the alkyl chain; aryl; alkoxy-substituted aryl, alkyl pyridyl and alkylpyridinium groups.

10. 12-(3'-hydroxypropyl) deoxoartemisinin.
11. 12-n-butyldeoxoartemisinin.
12. 12methylcyclopentyldeoxoartemisinin.
13. 12-cyclopentyldeoxoartemisinin.
14. 12-cyclohexyldeoxoartemisinin.
15. 12-(3'-dimethylaminopropyl) deoxoartemisinin.
16. 12-(3'-diethylaminopropyl) deoxoartemisinin.
17. 12-(2'-carboxyethyl) deoxoartemisinin.
18. 12-(carboxymethyl) deoxoartemisinin.
19. 12-(4'-carboxyphenethyl) deoxoartemisinin.
20. 12-(3'-carboxyphenethyl) deoxoartemisinin.
21. 12-phenyldeoxoartemisinin.
22. 12-(3',4'-dimethoxybenzyl) deoxoartemisinin.
23. 12-(3'pyridylmethyl) deoxoartemisinin.
24. N-(12-n-propyl deoxoartemisinin) pyridinium chloride.

* * * * *